United States Patent [19]
Chan et al.

[11] Patent Number: 5,919,981
[45] Date of Patent: Jul. 6, 1999

[54] CHIRAL AMINOPHOSPHINES

[75] Inventors: Albert Sun-Chi Chan; Fu-Yao Zhang, both of Kowloon, The Hong Kong Special Administrative Region of the People's Republic of China

[73] Assignee: The Hong Kong Polytechnic University, Kowloon, The Hong Kong Special Administrative Region of the People's Republic of China

[21] Appl. No.: 08/988,377

[22] Filed: Dec. 10, 1997

[51] Int. Cl.[6] .................................................. C07C 211/50
[52] U.S. Cl. ............................................................ 564/308
[58] Field of Search .............................................. 564/308

[56] References Cited

PUBLICATIONS

Kagan et al., "Reduction Asymetrique Catalysee Par Des Complexes De Metaux De Transition", Journal of Organometallic Chemistry, vol. 90, 1975, pp. 353–365.

Sinou et al., "Catalyse Asymetrique Par Le Complexe Cationique [Rh (COD) (+) Diop]*C10$_4$–", Journal of Organometallic Chemistry, vol. 114, 1976, pp. 325–337.

Samuel et al., "Phellanphos and Nopaphos, New Diphosphines for Asymmetric Catalysis", Nouveau Journal De Chimie, vol. 5, No. 1, 1981, pp. 15–20.

Burk et al., "A Convenient Asymmetric Synthesis of α–1–Arylalkylamines through the Enantioselective Hydrogenation of Enamides", J. Am. Chem. Soc., vol. 118, 1996, pp. 5142–5143.

*Primary Examiner*—Brian M. Burn
*Attorney, Agent, or Firm*—Leydig, Voit & Mayer

[57] ABSTRACT

This invention relates to (R)- and (S)-5,5',6,6',7,7',8,8'-octahydro-1,1'-binaphthyl-2,2'-diamine (R-1 and S-1) and (R)- and (S)-2,2'-bis(diarylphospinoamino)-5,5',6,6',7,7',8, 8'-octahydro-1,1'-binaphthyl (R-2 and S-2) and (R)- and (S)-2,2'-bis(dialkylphospinoamino)-5,5',6,6',7,7',8,8'-octahydro-1,1'-binaphthyl (R-3 and S-3); to a process for the preparation of R-1 and S-1 in which (R) or (S)-1,1'-binaphthyl-2,2'-diamine is partially hydrogenated in the presence of Adam's catalyst (5–20 wt % of starting material) at 20–100° C. for 20–100 hours in glacial acetic acid (solvent); to a process for the preparation of R-2, S-2, R-3 and S-3 in which R-1 or S-1 is reacted with chlorodiarylphosphine or chlorodialkylphosphine in the presence of n-butyllithium; and to the rhodium complexes containing 2 or 3 as effective catalysts for the asymmetric hydrogenation of prochiral substrates such as olefins to produce higher valued chiral products; and to the asymmetric catalytic hydrogenation of enamides under mild conditions using the Rh-(2) or Rh-(3) as catalyst with chemical yields as high as 100% and enantiomeric excess (e.e.) as high as 99%.

7 Claims, No Drawings

CHIRAL AMINOPHOSPHINES

FIELD OF INVENTION

This invention relates to a new class of organic compounds which are useful as auxiliaries in asymmetric synthesis for the production of a variety of chiral organic compounds, such as chiral amino acids, amides, and amines.

BACKGROUND

Chiral amines are an important class of organic compounds which can be used as resolving reagents, chiral auxiliaries, and intermediates in the synthesis of a variety of biologically active molecules. Asymmetric catalytic hydrogenation potentially provides a very efficient and convenient route to chiral amines; however, so far only limited success has been achieved. The well known chiral diphosphine ligands, such as, DIOP (*J. Organomet. Chem.* 1975, 90, 353) and its derivatives (*J. Organomet. Chem.* 1976, 114, 325), PHELLANPHOS and NOPAPHOS (*Nouv. J. Chim.* 1981, 5, 15), were used as chiral ligands in the asymmetric catalytic hydrogenation of α-phenylenamide. However, the enantiomeric excess (e.e.) values of the products were quite low. Recently, DUPHOS and BPE ligands (*J. Am. Chem. Soc.* 1996, 118, 5142) have been reported to be effective in the hydrogenation of arylenamides leading to high enantioselectivities (>90% e.e.). Unfortunately, with these catalysts the rate of reaction was too slow and the required reaction time was long.

SUMMARY OF THE INVENTION

We recently synthesized a class of novel aminophosphine ligands and surprisingly found that the rhodium catalysts containing this new class of aminophosphines were extremely active and enantioselective in the asymmetric hydrogenation of enamides. Quantitative chemical yields and up to 99% e.e. were obtained under very mild hydrogenation conditions (as low as one atmosphere of hydrogen pressure at 0° C. in 30–120 minutes). The catalysts were also highly active and enantioselective in the asymmetric hydrogenation of 2-acylamidoacrylic acids and their deritatives leading to high valued amino acids in high optical purity. The Preparation of the rhodium catalyst is convenient. All of these advantages make the novel aminophosphines attractive for industrial applications.

This present invention encompasses the hydrogenation reactions in which the catalyst thereof is a rhodium complex containing a chiral aminophosphine ligand of the present invention.

This present invention also relates to new chiral diamines R-1 and S-1, new chiral aminophosphines R-2, S-2, R-3 and S-3 and their synthetic routes.

The new chiral diamines of this invention have the following structures:

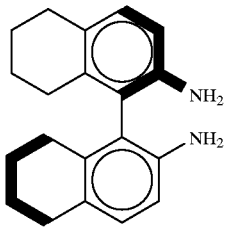

R-1

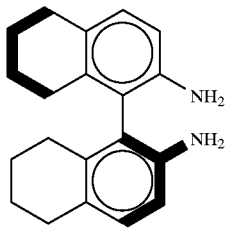

S-1

The novel, optically active ligands of this invention have the following structures:

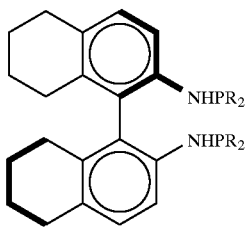

R-2 and R-3

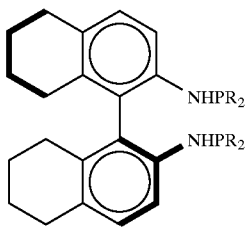

S-2 and S-3 wherein:

(a) for ligands R-2 and S-2, R is chosen from the following groups:

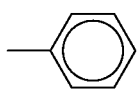

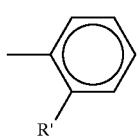

-continued

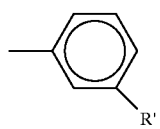

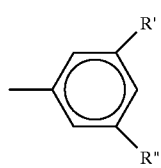

in which R' and R" are either the same or different with each representing a straight chain or branched alkyl group having from 1 to 6 carbon atoms or an alkoxyl group having from 1 to 6 carbon atoms; and (b) for ligands R-3 and S-3, R is a cycloalkyl group having from 5 to 8 carbon atoms.

The new chiral diamine R-1 or S-1 was synthesized by partial hydrogenation of (R)- or (S)-1,1-binaphthyl-2,2'-diamine and the new chiral ligand R-2, S-2, R-3 or S-3 was prepared by the reaction of the new chiral diamine R-1 or S-1 with chlorodiarylphosphine or chlorodialkylphosphine after treatment with n-butyllithium.

For the purposes of this invention, the catalysts can be prepared in situ by the reaction of the pure optical isomer of R-2, S-2, R-3 or S-3 with $[Rh(COD)Cl]_2$ (where COD represents cyclooctadiene) in a suitable organic solvent such as tetrahydrofuran (THF), acetone, benzene, etc. to produce the rhodium complex containing R-2, S-2, R-3 or S-3. The chloride anion can be replaced with a bromide or iodide ion. Alternatively, $AgBF_4$ can be added to the solution of Rh(COD)(2)Cl or Rh(COD)(3)Cl to produce $[Rh(COD)(2)]BF_4$ or $[Rh(COD)(3)]BF_4$, wherein (2) is the R-2 or S-2 and (3) is the R-3 or S-3 ligand. The $BF_4^-$ ion can be replaced by other non-coordinating or weakly coordinating anions such as $Cl_4^-$, $PF_6^-$, etc.

For the purposes of this invention, the rhodium complexes containing R-2, S-2, R-3 or S-3 can be used as catalysts in the hydrogenation of α-arylenamides and 2-acylamidoacrylic acids and their derivatives. Some illustrative examples of the precursors for the asymmetric hydrogenation are shown below:

α-Arylenamide:

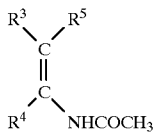

$R^3$=H, or=$CH_3$, $CH_2CH_3$, Ph, naphthyl, etc. when $R^5$=H
$R^4$=Ph, o-MePh, m-MePh, p-MePh, p-FPh, p-ClPh, p-$CF_3$Ph,

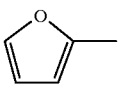

$R^5$=H, or=$CH_3$, $CH_2CH$, Ph, naphthyl, etc. when $R^3$=H
2-Acylamidoacrylic acid and its derivatives:

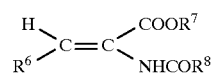

$R^6$=H, Ph, o-ClPh, m-ClPh, p-ClPh, p-BrPh, p-FPh, p-MeOPh, p-MePh, p-$NO_2$Ph,

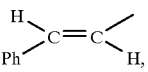

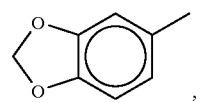

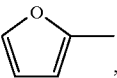

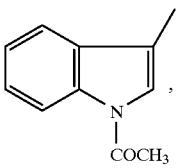

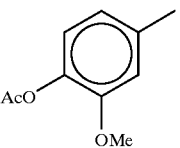

$R^7$–H, $CH_3$
$R^8$=$CH_3$, Ph

The following examples of experiments are provided to illustrate but not to limit the scope of the usefulness of this invention. In said examples, the following abbreviations are used: THF=tetrahydrofuran, COD=cyclooctadiene, e.e.= enantiomeric excess.

EXAMPLE 1

Preparation of (R)-5,5',6,6',7,7',8,8'-octahydro-1,1'-binaphthyl-2,2'-diamine (R-1): 200 mg (R)-1,1'-binaphthyl-2,2'-diamine (purchased from Aldrich Chemical Company), 20 mg $PtO_2$ and 20 mL glacial acetic acid were charged into a 50 mL autoclave equipped with a magnetic stirring bar. The autoclave was closed and 1,000 KPa hydrogen gas was charged. The solution was stirred with a magnetic stirrer for 120 hours at room temperature. After releasing the hydrogen gas and removing the solid catalyst by filtration, the mixture was neutralized with aqueous $NaHCO_3$ solution followed by extraction with 50 mL ethyl acetate three times. The combined extracts were dried with sodium sulfate and the solvent was removed with a rotary evaporator to give 210 mg of crude product (R-1). The crude product was purified by crystallization with 5 mL ethyl acetate and 15 mL hexane to give 180 mg crystals of R-1 (87.5% of theoretical yield). The analytical data for R-1 were as follows:

m.p.: 210° C. (decomposed); $[\alpha]_D=133°$ (c=1.0, pyridine); $^1$H-NMR (400 MHz, CDCl$_3$)δ: 1.61–1.73(m, 8H); 2.16–2.28(m, 4H); 2.70(m, 4H); 3.07(s, 4H); 6.60(d, J=8.2 Hz); 6.90(d, J=8.0 Hz). $^{13}$C-NMR (100 MHz,CDCl$_3$) δ: 23.6, 27.4, 29.7, 113.5, 122.4, 128.0, 129.6, 136.6, 141.9.

EXAMPLE 2

Preparation of (S)-5,5',6,6',7,7',8,8'-octahydro-1,1'-binaphthyl-2,2'-diamine (S-1): The procedure was the same as in example 1 except that (S)-1,1'-binaphthyl-2,2'-diamine was used as starting material instead of (R)-1,1'-binaphthyl-2,2'-diamine. The analytical data for S-1 were as follows:

m.p.: 210° C. (decomposed); $[\alpha]_D=-133°$ (c=1.0, pyridine); $^1$H-NMR (400 MHz, CDCl$_3$)δ: 1.61–1.73(m, 8H); 2.16–2.28(m, 4H); 2.70(m, 4H); 3.07(s, 4H); 6.60(d, J=8.2 Hz); 6.90(d, J=8.0 Hz). $^{13}$C-NMR (100 MHz, CDCl$_3$) δ: 23.6, 27.4, 29.7, 113.5, 122.4, 128.0, 129.6, 136.6, 141.9.

EXAMPLE 3

Preparation of (R)-2,2'-bis(diphenylphospinoamino)-5,5',6,6',7,7',8,8'-octahydro-1,1'-binaphthyl (R-2a): (R)-5,5'6,6',7,7',8,8'-octahydro-1,1'-binaphthyl-2,2'-diamine (R-1) (200 mg, 0.7 mmol) in THF (20 mL) was charged to a 50 mL flask under a dinitrogen atmosphere. This flask was cooled to −30° C. and into the solution was added a solution of n-butyllithium in hexane (0.88 mL of 1.6 M solution, 1.4 mmol) in a dropwise manner. The mixture was stirred for two hours at −30° C. with a magnetic stirrer. Then a solution of chlorodiphenylphosphine (0.32 mL, 1.8 mmol) in THF (5 mL) was added dropwise. The system was allowed to stir for 5 hours and the temperature was raised to room temperature. The solution was filtered to remove the solid. The THF solvent was removed in vacuo to give 420 mg of R-2a. The crude product was dissolved in 2 mL dichloromethane and 10 mL of diethyl ether was added to the solution. The final solution was kept at −30° C. for 24 hours to allow the growth of pure crystals of R-2a. After filtration and drying in vacuo, 390 mg of white, needle-like crystals of R-2a were obtained (85% of theoretical yield). The analytical data for R-2a were as follows:

m.p.: 137–139° C.; $[\alpha]_D=31\ 47°$ (c=1.0, CH$_2$Cl$_2$); $^1$H-NMR (400 MHz, CDCl$_3$)δ: 1.58(m, 8H); 2.10(m, 4H); 2.67(m, 4H); 4.27(d, J$_{P-H}$=7.0 Hz, 2H); 6.98(d, J$_{H-H}$=8.34 Hz, 2H); 7.24(m, 22H). $^{13}$C-NMR (100 MHz, CDCl$_3$)δ: 23.0, 23.1, 27.3, 29.3, 112.5, 112.7, 123.2, 128.2, 128.3, 128.4, 128.7, 128.9, 129.6, 130.2, 130.4, 130.8, 131.0, 136.1, 140.5, 140.6, 141.0, 141.2, 141.7, 141.9. $^{31}$P-NMR (160 MHz, CDCl$_3$) δ: 27.25 ppm.

EXAMPLE 4

Preparation of (S)-2,2'-bis(diphenylphospinoamino)-5,5',6,6',7,7',8,8'-octahydro-1,1'-binaphthyl (S-2a): The procedure was the same as in example 3 except that (S)-5,5',6,6',7,7',8,8'-octahydro-1,1'-binaphthyl-2,2'-diamine (S-1) was used as starting material instead of (R)-5,5',6,6',7,7',8,8'-octahydro-1,1'-binaphthyl-2,2'-diamine (R-1). The analytical data for S-2a were as follows:

m.p.: 137–139° C.; $[\alpha]_D=47°$ (c=1.0, CH$_2$Cl$_2$); $^1$H-NMR (400 MHz, CDCl$_3$)δ: 1.58(m, 8H); 2.10(m, 4H); 2.67(m, 4H); 4.27(d, J$_{P-H}$=7.0 Hz, 2H); 6.98(d, J$_{H-H}$=8.34 Hz, 2H); 7.24(m, 22H). $^{13}$C-NMR (100 MHz, CDCl$_3$)δ: 23.0, 23.1, 27.3, 29.3, 112.5, 112.7, 123.2, 128.2, 128.3, 128.4, 128.7, 128.9, 129.6, 130.2, 130.4, 130.8, 131.0, 136.1, 140.5, 140.6, 141.0, 141.2, 141.7, 141.9. $^{31}$P-NMR (160 MHz, CDCl$_3$) δ: 27.25 ppm.

EXAMPLE 5

Preparation of [Rh(COD)(R-2a)]BF$_4$ complex: [Rh(COD)Cl]$_2$ (purchased from Stream Chemicals, Inc., Newburyport, Mass.) (5.0 mg, 0.01 mmol) and AgBF$_4$(4.0 mg, 0.03 mmol) in THF (2 mL) were stirred at room temperature for 30 minutes under nitrogen atmosphere. The solution was filtered to remove the solid AgCl. After the addition of R-2a (13 mg, 0.02 mmol) in THF (3 mL) to the solution, [Rh(COD)(R-2a)]BF$_4$ in THF was obtained in situ (4×10$^{-6}$ mol/mL). $^{31}$P-NMR (160 MHz, THF): 63.45(d, J$_{Rh-P}$=155.1 Hz).

EXAMPLE 6

Preparation of [Rh(COD)(S-2a)]BF$_4$ complex: The THF solution of [Rh(COD)(S-2a)]BF$_4$ (4×10$^{-6}$ mol/mL) was prepared in situ with the same procedure as in example 5 by using S-2a instead of R-2a. $^{31}$P-NMR (160 MHz, THF): 63.45(d, J$_{Rh-P}$=155.1 Hz).

EXAMPLE 7

Asymmetric hydrogenation of N-acetyl-1-phenylethenamine catalyzed by [Rh(COD)(R-2a)]BF$_4$ complex at 0° C.: A THF solution of [Rh(COD)(R-2a)]BF$_4$ (300 μL, 0.0012 mmol) (prepared in example 5) and N-acetyl-1-phenylethenamine (0.039 g, 0.24 mmol) in THF(10 mL) were charged to a 50 mL autoclave. The hydrogenation was carried out under 100 KPa of hydrogen pressure at 0° C. for 30 minutes. A portion of the reaction mixture was analyzed by gas chromatography to determine the product composition. Complete conversion (100%) of the starting material to the hydrogenation product and 96.8% e.e. of (R)-N-acetyl-1-phenylethylamine were observed. Activated carbon (5 mg) was added to the solution and the mixture was stirred for 15 minutes. After filtration, the THF solvent was evaporated to give a white solid of (R)-N-acetyl-1-phenylethylamine (0.038 g), 96.8% e.e., yield 97% (The enantiomeric excess was determined by chiral capillary GC using a Chrompack Chirasil-L-Val column.)

EXAMPLE 8

Asymmetric hydrogenation of N-acetyl-1-phenylethenamine catalyzed by [Rh(COD)(S-2a)]BF$_4$ complex at 0° C.: The hydrogenation was carried out through the same procedure as in example 7 using [Rh(COD)(S-2a)]BF$_4$ (prepared in example 6) instead of [Rh(COD)(R-2a)]BF$_4$ (prepared in example 5) to give the product (S)-N-acetyl-1-phenylethylamine, 96.8% e.e., 97% yield (The enantiomeric excess was determined by chiral capillary GC using a Chrompack Chirasil-L-Val column.)

EXAMPLE 9

Asymmetric hydrogenation of N-acetyl-1-phenylethenamine catalyzed by [Rh(COD)(R-2a)]BF$_4$ complex at room temperature: The hydrogenation was carried out through the same procedure as in example 7 at room temperature (25° C.) instead of 0° C. to give the product (R)-N-acetyl-1-phenylethylamine in 92.1% e.e., 98% yield (The enantiomeric excess was determined by chiral capillary GC using a Chrompack Chirasil-L-Val column.)

EXAMPLE 10

Asymmetric hydrogenation of N-acetyl-1-phenylethenamine catalyzed by [Rh(COD)(S-2a)]BF$_4$ complex at room temperature: The hydrogenation was carried out through the same procedure as in example 7 at room temperature instead of 0° C. to give the product (S)-N-acetyl-1-phenylethylamine, 92.4% e.e., 98% yield (The enantiomeric excess was determined by chiral capillary GC using a Chrompack Chirasil-L-Val column.)

EXAMPLE 11

Asymmetric hydrogenation of E/Z isomers (3:2) of N-acetyl-1-(4'-chlorophenyl)-propenamine catalyzed by [Rh(COD)(R-2a)]BF$_4$ complex at 0° C.: THF solution of [Rh(COD)(R-2a)]BF$_4$ (300 μL, 0.0012 mmol) (prepared in example 5) and N-acetyl-1-(4'-chlorophenyl)-propenamine (0.047 g, 0.24 mmol) in THF(10 mL) were charged to a 50 mL autoclave. The hydrogenation was carried out under 100 KPa of hydrogen pressure at 0° C. for 2 hours. A portion of the reaction mixture was analyzed by gas chromatography to determine the product composition. Complete conversion (100%) of the starting material to the hydrogenation product and 80.3% e.e. of (R)-N-acetyl-1-(4'-chlorophenyl)propylamine were observed. Activated carbon (5 mg) was added to the solution and the mixture was stirred for 15 minutes. After filtration, the THF solvent was evaporated to give a white solid of (R)-N-acetyl-1-(4'-chlorophenyl)propylamine (0.045 g), 80.3% e.e., yield 96% (The enantiomeric excess was determined by chiral capillary GC using a Chrompack Chirasil-L-Val column.)

EXAMPLE 12

Asymmetric hydrogenation of E/Z isomers (3:2) of N-acetyl-1-(4'-chlorophenyl)-propenamine catalyzed by [Rh(COD)(S-2a)]BF$_4$ complex at 0° C.: The hydrogenation was carried out through the same procedure as in example 11 using [Rh(COD)(S-2a)]BF$_4$ (prepared in example 6) instead of [Rh(COD)(R-2a)]BF$_4$ (prepared in example 5) to give the product (S)-N-acetyl-1-(4'-chlorophenyl)propylamine, 80.2% e.e., 96% yield (The enantiomeric excess was determined by chiral capillary GC using a Chrompack Chirasil-L-Val column.)

EXAMPLE 13

Asymmetric hydrogenation of methyl (Z)-2-acetamidocinnamate catalyzed by [Rh(COD)(R-2a)]BF$_4$ complex at room temperature: A THF solution of [Rh(COD)(R-2a)]BF$_4$ (600 μL, 0.0024 mmol) (prepared in example 5) and methyl (Z)-2-acetamidocinnamate (0.053 g, 0.24 mmol) in THF(10 mL) were charged to a 50 mL autoclave. The hydrogenation was carried out under 200 KPa of hydrogen pressure at room temperature for 10 minutes. A portion of the reaction mixture was analyzed by gas chromatography to determine the product composition. 100% conversion of the starting material to the hydrogenation product and 95.8% e.e. of methyl (R)-2-acetamido-3-phenylpropionate were observed. Activated carbon (5 mg) was added to the solution and the mixture was stirred for 15 minutes. After filtration, the THF solvent was evaporated to give a white solid of methyl (R)-2-acetamido-3-phenylpropanoate (0.050 g), 95.8% e.e., yield 95% (The enantiomeric excess was determined by chiral capillary GC using a Chrompack Chirasil-L-Val column.)

EXAMPLE 14

Asymmetric hydrogenation of methyl (Z)-2-acetamidocinnamate catalyzed by [Rh(COD)(S-2a)]BF$_4$ complex at room temperature: The hydrogenation was carried out through the same procedure as in example 13 at room temperature except that [Rh(COD)(S-2a)]BF$_4$ was used as catalyst instead of [Rh(COD)(R-2a)]BF$_4$ to give the product methyl (S)-2-acetamido-3-phenylpropionate in 95.6% e.e., 95% yield (The enantiomeric excess was determined by chiral capillary GC using a Chrompack Chirasil-L-Val column.)

EXAMPLE 15

Asymmetric hydrogenation of N-acetamidoacrylic acid catalyzed by [Rh(COD)(R-2a)]BF$_4$ complex at room temperature: A THF solution of [Rh(COD)(R-2a)]BF$_4$ (600 μL, 0.0024 mmol) (prepared in example 5) and N-acetamidoacrylic acid (0.031 g, 0.24 mmol) in ethanol (10 mL) were charged to a 50 mL autoclave. The hydrogenation was carried out under 200 KPa of hydrogen pressure at room temperature for 10 minutes. A portion of the reaction mixture was analyzed by gas chromatography to determine the product composition. 100% conversion of the starting material to the hydrogenation product and 99.0% e.e. of (R)-acetamidopropionic acid were observed. Activated carbon (2 mg) was added to the solution and the mixture was stirred for 15 minutes. After filtration, the solvent was evaporated to give a white solid of (R)-acetamido-propionic acid (0.029 g), 99.0% e.e., yield 94% (The enantiomeric excess was determined by chiral capillary GC using a Chrompack Chirasil-L-Val column after converting the product to methyl ester.)

EXAMPLE 16

Asymmetric hydrogenation of N-acetamidoacrylic acid catalyzed by [Rh(COD)(S-2a)]BF$_4$ complex at room temperature: The hydrogenation was carried out through the same procedure as in example 15 at room temperature except that [Rh(COD)(S-2a)]BF$_4$ as catalyst was used instead of [Rh(COD)(R-2a)]BF$_4$ to give the product (S)-acetamidopropionic acid, 99.0% e.e., 94% yield (The enantiomeric excess was determined by chiral capillary GC using a Chrompack Chirasil-L-Val column after converting the product to methyl ester.)

EXAMPLE 17

Other examples of hydrogenation of enamides are shown below:

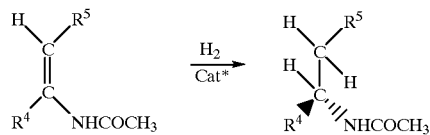

| Entry | R⁴ | R⁵ | Cat. | T (°C.) | Time (min) | Conv. (%) | e.e. (%) | Confi |
|---|---|---|---|---|---|---|---|---|
| 1 | $C_6H_5$ | H | $[Rh(COD)(R\text{-}2a)]BF_4$ | RT | 10 | 100 | 92.1 | R |
| 2 | $C_6H_5$ | H | $[Rh(COD)(S\text{-}2a)]BF_4$ | RT | 10 | 100 | 92.1 | S |
| 3 | $C_6H_5$ | H | $[Rh(COD)(R\text{-}2a)]BF_4$ | 0 | 30 | 100 | 96.8 | R |
| 4 | $C_6H_5$ | H | $[Rh(COD)(S\text{-}2a)]BF_4$ | 0 | 30 | 100 | 96.8 | S |
| 5 | $p\text{-}CF_3C_6H_4$ | H | $[Rh(COD)(R\text{-}2a)]BF_4$ | RT | 10 | 100 | 97.5 | R |
| 6 | $p\text{-}CF_3C_6H_4$ | H | $[Rh(COD)(R\text{-}2a)]BF_4$ | 0 | 30 | 100 | 99.0 | R |
| *7 | $p\text{-}CF_3C_6H_4$ | H | $[Rh(COD)(R\text{-}2a)]BF_4$ | 0 | 30 | 100 | 98.7 | R |
| 8 | $p\text{-}FC_6H_4$ | H | $[Rh(COD)(R\text{-}2a)]BF_4$ | RT | 10 | 100 | 89.6 | R |
| 9 | $p\text{-}FC_6H_4$ | H | $[Rh(COD)(R\text{-}2a)]BF_4$ | 0 | 30 | 100 | 96.0 | R |
| 10 | $m\text{-}CH_3C_6H_4$ | H | $[Rh(COD)(R\text{-}2a)]BF_4$ | RT | 10 | 100 | 92.0 | R |
| 11 | $m\text{-}CH_3C_6H_4$ | H | $[Rh(COD)(R\text{-}2a)]BF_4$ | 0 | 30 | 100 | 97.7 | R |
| 12 | $p\text{-}CH_3C_6H_4$ | H | $[Rh(COD)(R\text{-}2a)]BF_4$ | RT | 10 | 100 | 93.2 | R |
| 13 | $p\text{-}CH_3C_6H_4$ | H | $[Rh(COD)(R\text{-}2a)]BF_4$ | 0 | 30 | 100 | 97.0 | R |
| 14 | $p\text{-}ClC_6H_4$ | H | $[Rh(COD)(R\text{-}2a)]BF_4$ | RT | 10 | 100 | 94.0 | R |
| 15 | $p\text{-}ClC_6H_4$ | H | $[Rh(COD)(R\text{-}2a)]BF_4$ | 0 | 30 | 100 | 97.0 | R |
| 16 | 2-furanyl | H | $[Rh(COD)(R\text{-}2a)]BF_4$ | RT | 10 | 100 | 97.4 | R |
| 17 | 2-furanyl | H | $[Rh(COD)(R\text{-}2a)]BF_4$ | 0 | 30 | 100 | 98.4 | R |
| 18 | $C_6H_5$ | $CH_3$ | $[Rh(COD)(R\text{-}2a)]BF_4$ | 0 | 120 | 83.4 | 78.3 | R |
| 19 | $p\text{-}CH_3C_6H_4$ | $CH_3$ | $[Rh(COD)(R\text{-}2a)]BF_4$ | 0 | 120 | 96.6 | 76.9 | R |
| 20 | $p\text{-}ClC_6H_4$ | $CH_3$ | $[Rh(COD)(R\text{-}2a)]BF_4$ | 0 | 120 | 100 | 80.3 | R |

Substrate/Catalyst (mole/mole) = 200;
$P_{H2}$ = 100 KPa;
THF as solvent.
*Substrate/Catalyst (mole/mole) = 1000.
The conversion and e.e. values were determined by GLC with a CHIRASIL-L-VAL column.

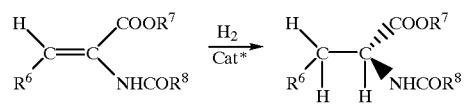

| Entry | R⁶ | R⁸ | R⁷ | Cat. | Conv. (%) | e.e. (%) | Config. |
|---|---|---|---|---|---|---|---|
| 1 | phenyl | $CH_3$ | $CH_3$ | $[Rh(COD)(R\text{-}2a)]BF_4$ | 100 | 95.8 | R |
| 2 | H | $CH_3$ | $CH_3$ | $[Rh(COD)(R\text{-}2a)]BF_4$ | 100 | 97.1 | R |
| 3 | o-chloro-phenyl | $CH_3$ | $CH_3$ | $[Rh(COD)(R\text{-}2a)]BF_4$ | 100 | 97.0 | R |
| 4 | m-chloro-phenyl | $CH_3$ | $CH_3$ | $[Rh(COD)(R\text{-}2a)]BF_4$ | 100 | 94.0 | R |
| 5 | p-chloro-phenyl | $CH_3$ | $CH_3$ | $[Rh(COD)(R\text{-}2a)]BF_4$ | 100 | 94.0 | R |
| 6 | 4-bromo-phenyl | $CH_3$ | $CH_3$ | $[Rh(COD)(R\text{-}2a)]BF_4$ | 100 | 95.5 | R |
| 7 | 4-bromo-phenyl | phenyl | $CH_3$ | $[Rh(COD)(R\text{-}2a)]BF_4$ | 100 | 96.4 | R |
| 8 | 4-fluoro-phenyl | $CH_3$ | $CH_3$ | $[Rh(COD)(R\text{-}2a)]BF_4$ | 100 | 92.9 | R |
| 9 | 4-fluoro-phenyl | phenyl | $CH_3$ | $[Rh(COD)(R\text{-}2a)]BF_4$ | 100 | 94.2 | R |
| 10 | 4-methoxy-phenyl | $CH_3$ | $CH_3$ | $[Rh(COD)(R\text{-}2a)]BF_4$ | 100 | 93.1 | R |
| 11 | 4-methoxy-phenyl | phenyl | $CH_3$ | $[Rb(COD)(R\text{-}2a)]BF_4$ | 100 | 95.2 | R |
| 12 | p-methyl-phenyl | $CH_3$ | $CH_3$ | $[Rh(COD)(R\text{-}2a)]BF_4$ | 100 | 94.4 | R |
| 13 | p-methyl-phenyl | phenyl | $CH_3$ | $[Rh(COD)(R\text{-}2a)]BF_4$ | 100 | 94.6 | R |
| 14 | 4-nitro-phenyl | $CH_3$ | $CH_3$ | $[Rh(COD)(R\text{-}2a)]BF_4$ | 100 | 90.7 | R |
| 15 | 3,4-methylene-dioxyphenyl | $CH_3$ | $CH_3$ | $[Rh(COD)(R\text{-}2a)]BF_4$ | 100 | 92.6 | R |
| 16 | trans-cinnamyl | $CH_3$ | $CH_3$ | $[Rh(COD)(R\text{-}2a)]BF_4$ | 100 | 90.0 | R |
| 17 | 2-furyl | $CH_3$ | $CH_3$ | $[Rh(COD)(R\text{-}2a)]BF_4$ | 100 | 90.0 | R |
| 18 | 2-furyl | phenyl | $CH_3$ | $[Rh(COD)(R\text{-}2a)]BF_4$ | 100 | 93.2 | R |
| 19 | N-aceto-3-indole | phenyl | $CH_3$ | $[Rh(COD)(R\text{-}2a)]BF_4$ | 100 | 92.5 | R |

Substrate/Catalyst (mole/mole) = 100;
$P_{H2}$ = 200 KPa;
room temperature;
time = 10 min;
THF as solvent
The conversion and e.e. values were determined by GLC with a CHIRASIL-L-VAL column.

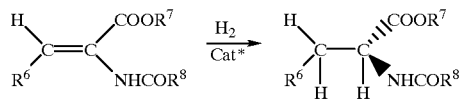

| Entry | R[6] | R[8] | R[7] | Cat. | Conv. (%) | e.e. (%) | Config. |
|---|---|---|---|---|---|---|---|
| 1 | phenyl | CH$_3$ | H | [Rh(COD)(R-2a)]BF$_4$ | 100 | 94.2 | R |
| 2 | H | CH$_3$ | H | [Rh(COD)(R-2a)]BF$_4$ | 100 | 99.0 | R |
| 3 | o-chloro-phenyl | CH$_3$ | H | [Rh(COD)(R-2a)]BF$_4$ | 100 | 94.1 | R |
| 4 | m-chloro-phenyl | CH$_3$ | H | [Rh(COD)(R-2a)]BF$_4$ | 100 | 92.8 | R |
| 5 | p-chloro-phenyl | CH$_3$ | H | [Rh(COD)(R-2a)]BF$_4$ | 100 | 93.1 | R |
| 6 | 2-methoxy-phenyl | CH$_3$ | H | [Rh(COD)(R-2a)]BF$_4$ | 100 | 92.5 | R |
| 7 | 4-nitro-phenyl | CH$_3$ | H | [Rh(COD)(R-2a)]BF$_4$ | 100 | 90.0 | R |
| 8 | 3,4-methylene-dioxyphenyl | CH$_3$ | H | [Rh(COD)(R-2a)]BF$_4$ | 100 | 91.1 | R |
| 9 | 2-furyl | phenyl | H | [Rh(COD)(R-2a)]BF$_4$ | 100 | 93.9 | R |

Substrate/Catalyst (mole/mole) = 100;
$P_{H2}$ = 200 KPa;
room temperature;
time = 10 min;
ethanol as solvent.
The conversion and e.e. values were determined by GLC with a CHIRASIL-L-VAL column after converting to its methyl ester derivative.

We claim:

1. A chiral diamine R-1 or S-1 having the following structures:

R-1

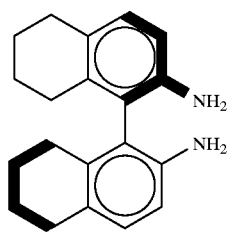

S-1

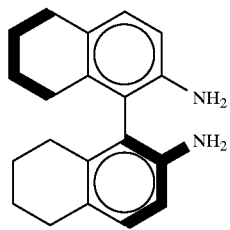

2. A process for the preparation of the chiral diamines of to claim 1 comprising partial hydrogenation of (R)- or (S)-1,1'-binaphthyl-2,2'-diamine in the presence of Adam's catalyst.

3. The process according to claim 2 wherein the amount of Adam's catalyst used is from 5–20 wt. % of the amount of (R)- or (S)-1,1'-binaphthyl-2,2'-diamine used.

4. The process according to claim 2 wherein the hydrogen pressure is from 500 to 3000 KPa.

5. The process according to claim 2 wherein the hydrogenation is conducted at a temperature of from 20–100° C. for from 20 to 100 hours in glacial acetic acid as a solvent.

6. The process according to claim 2 wherein the hydrogenation is conducted at room temperature for 48 hours, using glacial acetic acid as a solvent, at a hydrogen pressure of 500–1000 KPa and in which the amount of Adam's catalyst used is 10 wt. % of the amount of (R)- or (S)-1,1'-binaphthyl-2,2'-diamine used.

7. The chiral diamine of claim 1, wherein the chiral diamine comprises R-1.

* * * * *